United States Patent
Ritchart et al.

[11] Patent Number: 5,913,857
[45] Date of Patent: Jun. 22, 1999

[54] METHODS AND DEVICES FOR COLLECTION OF SOFT TISSUE

[75] Inventors: Mark A. Ritchart, Murrieta; Minh Tran, Westminster, both of Calif.

[73] Assignee: Ethicon End0-Surgery, Inc., Cincinnati, Ohio

[21] Appl. No.: 08/786,497

[22] Filed: Jan. 21, 1997

Related U.S. Application Data

[63] Continuation-in-part of application No. 08/705,622, Aug. 29, 1996, Pat. No. 5,810,806.

[51] Int. Cl.$^6$ .................................................. A61B 17/32
[52] U.S. Cl. ................................. 606/45; 604/22; 606/46
[58] Field of Search ........................... 606/41, 42, 45–50; 604/21, 22; 607/100–105

[56] References Cited

U.S. PATENT DOCUMENTS

| | | | |
|---|---|---|---|
| 2,113,246 | 4/1938 | Wappler | 606/205 |
| 3,850,162 | 11/1974 | Iglesias | 606/46 |
| 4,325,374 | 4/1982 | Komiya | 606/47 |
| 4,362,160 | 12/1982 | Hiltebrandt . | |
| 5,014,708 | 5/1991 | Hayashi et al. . | |
| 5,047,027 | 9/1991 | Rydell . | |
| 5,064,424 | 11/1991 | Bitrolf . | |
| 5,078,716 | 1/1992 | Doll | 606/47 |
| 5,133,360 | 7/1992 | Spears . | |
| 5,133,713 | 7/1992 | Huang et al. | 606/46 |
| 5,159,925 | 11/1992 | Neuwirth et al. | 606/28 |
| 5,186,714 | 2/1993 | Boudreault et al. | 606/49 |
| 5,201,731 | 4/1993 | Hakky . | |
| 5,201,741 | 4/1993 | Dulebohn | 606/47 |
| 5,282,800 | 2/1994 | Foshee et al. | 606/52 |
| 5,304,176 | 4/1994 | Phillips | 606/41 |
| 5,312,327 | 5/1994 | Bales et al. . | |
| 5,334,183 | 8/1994 | Wuchinich . | |
| 5,348,555 | 9/1994 | Zinnanti . | |
| 5,395,312 | 3/1995 | Desai | 606/45 |
| 5,403,311 | 4/1995 | Abele et al. . | |
| 5,437,665 | 8/1995 | Munro | 606/47 |
| 5,441,503 | 8/1995 | Considine et al. | 606/46 |

FOREIGN PATENT DOCUMENTS

| | | |
|---|---|---|
| 0 593 929 A1 | 4/1994 | European Pat. Off. . |
| 31 48 306 A1 | 6/1983 | Germany . |
| WO 89/10092 | 11/1989 | WIPO . |
| WO 95/08291 | 3/1995 | WIPO . |

*Primary Examiner*—Michael Peffley

[57] ABSTRACT

This invention provides an inventive tissue sampling probe which offers many advantages over probes available in the prior art. Unexpectedly superior results are obtained in connection with the retrieval of intact tissue specimens, because of a unique combination of cutting features, including, in particular, the employment of an electrosurgical cutting element which is extendible to permit ready severance of the distal end of the tissue specimen, without impact to surrounding tissue. Additionally, the inventive instrument is advantageously designed so that portions of the instrument which contact the patient's tissue or fluid discharge (i.e. blood) during a procedure are modular and disposable, to permit ready replacement of those portions with a new module for an ensuing procedure, without the necessity of cleaning and sterilizing the instrument. The versatility of the invention permits its use in many applications, including, for example, breast biopsies, intraoperative staging, laparoscopic surgery, and lymphadenectomy procedures.

20 Claims, 7 Drawing Sheets

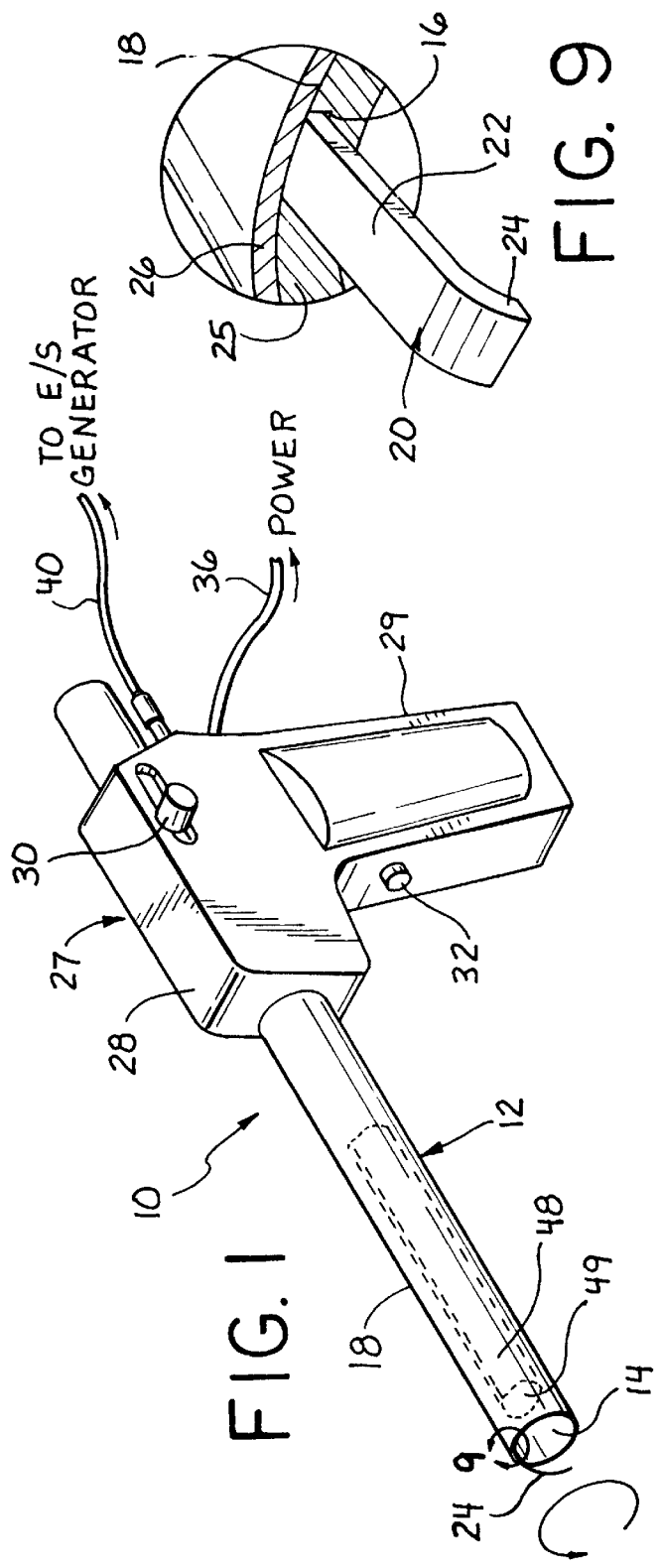
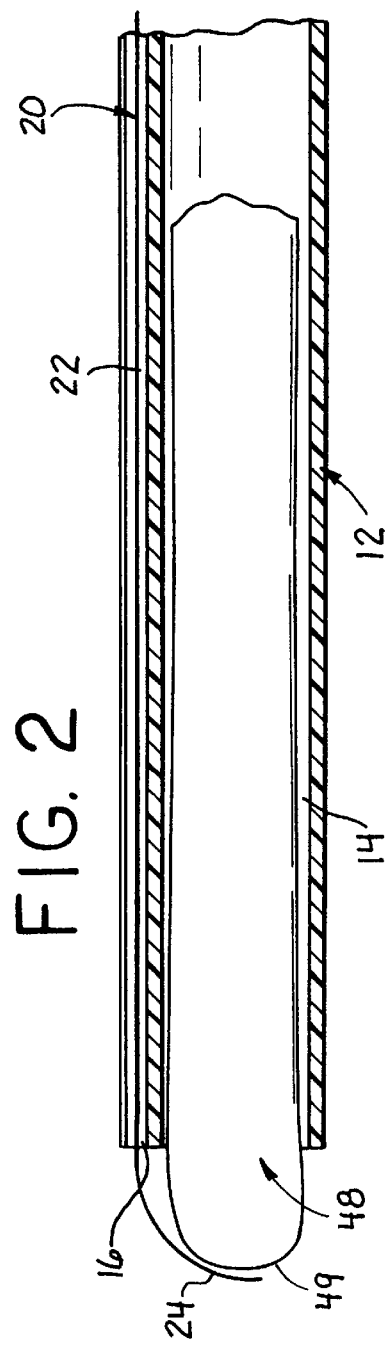

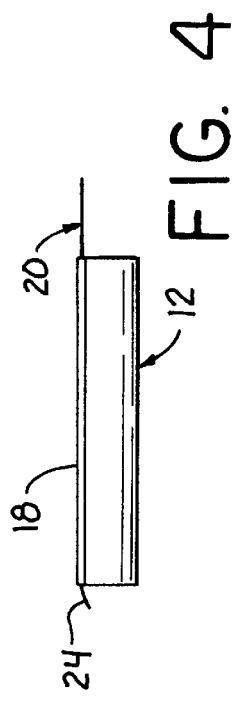
FIG. 3
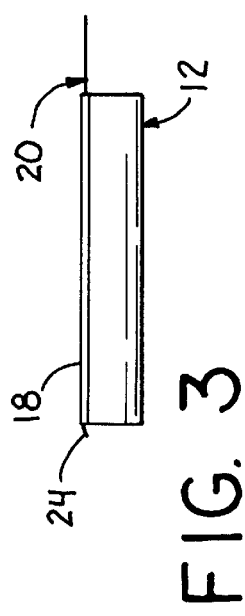
FIG. 4
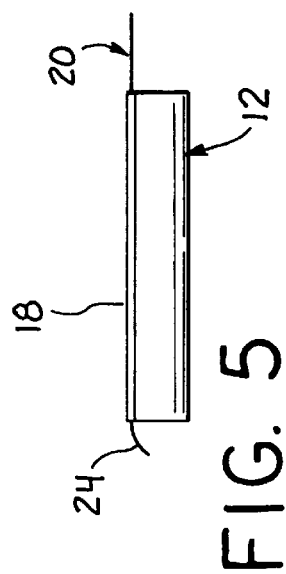
FIG. 5
FIG. 6
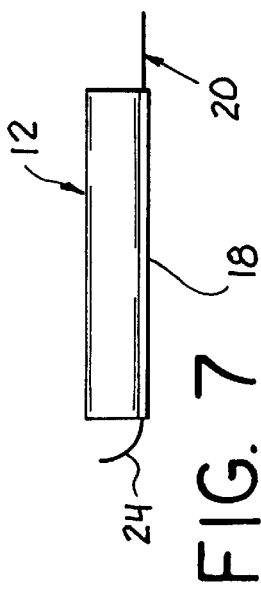
FIG. 7
FIG. 8

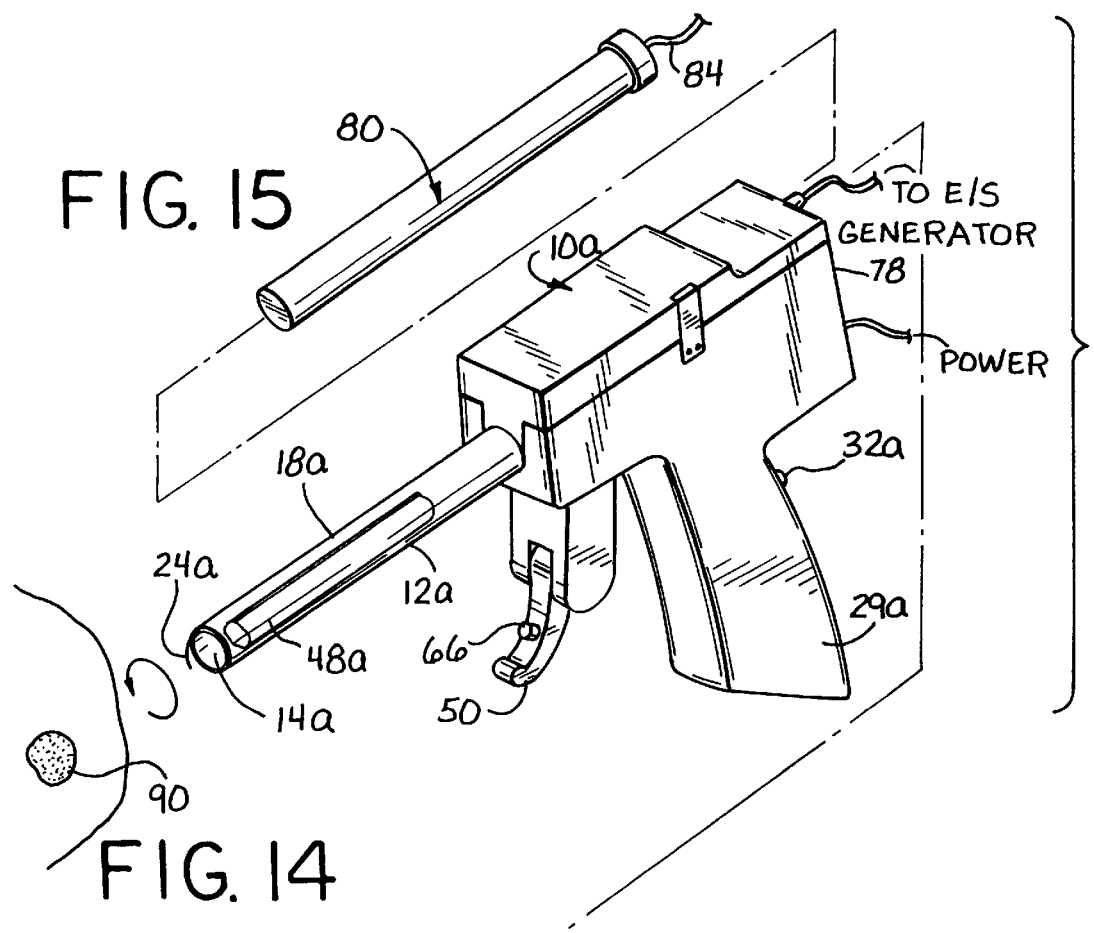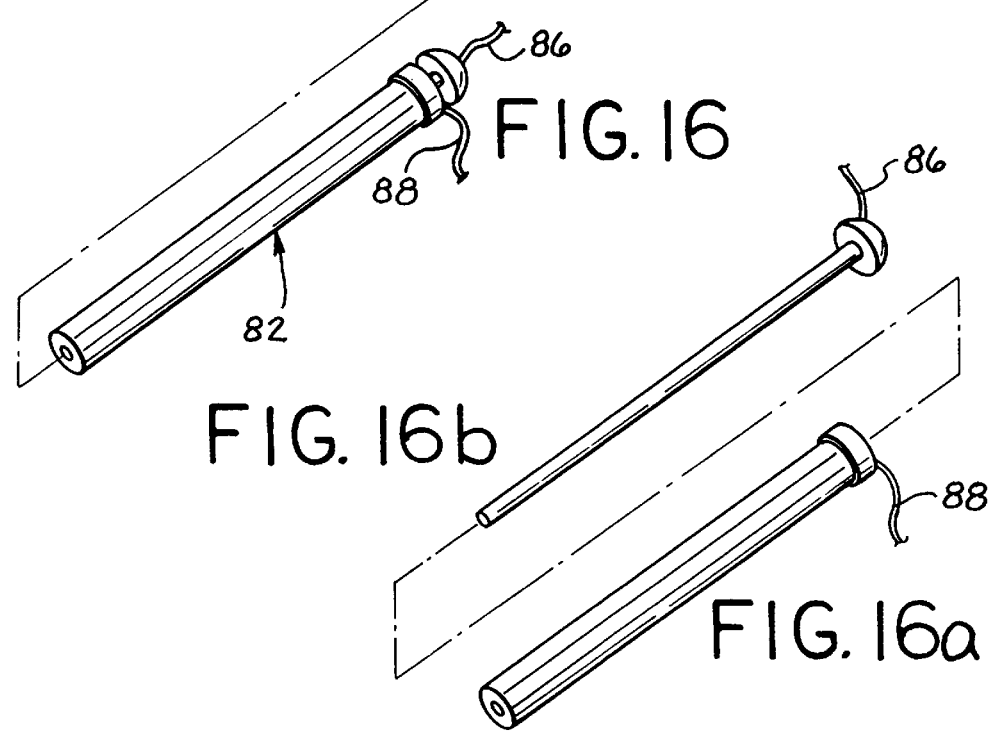

METHODS AND DEVICES FOR COLLECTION OF SOFT TISSUE

CROSS-REFERENCE TO THE RELATED APPLICATIONS

This application is a continuation-in-part of application Ser. No. 08/705,622, filed on Aug. 29, 1996, U.S. Pat. No. 5,810,806.

FIELD OF THE INVENTION

The present invention relates to methods and devices for tissue sampling, and more specifically to improved instruments and methods for acquiring soft body tissue.

BACKGROUND OF THE INVENTION

It is often desirable and frequently necessary to sample or test a portion of tissue from humans and other animals, particularly in the diagnosis and treatment of patients with cancerous tumors, pre-malignant conditions, and other diseases or disorders.

Typically, in the case of breast cancer, there is a great emphasis on early detection and diagnosis through the use of screening modalities, such as physical examination, and particularly mammography, which is capable of detecting very small abnormalities, often nonpalpable. When the physician establishes by means of a mammogram or other screening modality that suspicious circumstances exist, a biopsy must be performed to capture tissue for a definitive diagnosis as to whether the suspicious lesion is cancerous. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, including the location of the lesion(s) within the body, and no single procedure is ideal for all cases. However, core biopsy is extremely useful in a number of conditions and is being used more frequently by the medical profession.

A very successful type of image guided percutaneous core breast biopsy instrument currently available is a vacuum-assisted automatic core biopsy device. One such successful biopsy device is shown and disclosed in U.S. Pat. No. 5,526,822, U.S. patent application Ser. No. 08/386,941, filed on Feb. 10, 1995, and U.S. pat. application Ser. No. 08/568,143, filed on Dec. 6, 1995, all of which are commonly owned by the assignee of the present application and are herein incorporated by reference. This device, known commercially as the MAMMOTOME® Biopsy System, has the capability to actively capture tissue prior to cutting the tissue. Active capture allows for sampling through non-homogeneous tissues, meaning that the device is equally capable of cutting through hard and soft tissue. The device is comprised of a disposable probe, a motorized drive unit, and an integrated vacuum source. The probe is made of stainless steel and molded plastic and is designed for collection of multiple tissue samples with a single insertion of the probe into the tissue. The tip of the probe is configured with a laterally disposed sampling notch for capturing tissue samples. Orientation of the sample notch is directed by the physician, who uses a thumbwheel to direct tissue sampling in any direction about the circumference of the probe. A hollow cylindrical cutter severs and transports tissue samples to a tissue collection chamber for later testing.

While the MAMMOTONE Biopsy System functions very well as a core biopsy device, there are occasions when, because of the size of a lesion, or its location, it may be advantageous to use a core biopsy device of a type disclosed in U.S. Pat. No. 5,111,828, to Kornberg et al., also expressly incorporated by reference herein, wherein the tissue receiving port is disposed at the distal end of the device and is oriented axially rather than laterally. A disadvantage of this type of device, however, is the lack of ability to effectively and efficiently draw tissue into the receiving chamber prior to and during the tissue cutting process. A second disadvantage is the requirement to withdraw the device from parent tissue and remove the first specimen, reassemble the device, then reintroduce the device for each desired specimen. A third disadvantage is the necessity of manually handling each specimen obtained.

On other occasions, the ability to sample any selected area of a cavity wall from within the cavity may be important, which ability requires the use of a flexible probe.

Furthermore, it is desirable during the biopsy process to "stage" the spread of a cancer. For example, breast cancer starts in the milk ducts, the mammary glands. The initial change towards breast cancer is now thought to be the development of atypical ductal hyperplasia. The next step is thought to be represented by ductal carcinoma in situ. Finally, the last step in the development of breast cancer is infiltrating ductal carcinoma. By the time the breast cancer has reached the stage of infiltrative ductal carcinoma, breast cancer cells have developed the ability to migrate from the duct of origin, disassociate themselves from one another, and enter vascular structures, such as the lymphatic channels. When these malignant infiltrative ductal carcinoma cells enter the vascular system, they can spread or metastasize to other parts of the body. It is this metastatic process that ultimately leads to death from breast cancer.

When breast cancer cells enter the lymphatic system, they metastasize in an orderly fashion to regional lymph nodes. Drainage can occur to the axillary lymph nodes, the supraclavicular lymph nodes, the lateral thoracic lymph nodes, and to the internal mammary lymph nodes.

It is the current standard of practice to determine if breast cancer cells have extended to regional lymph nodes by surgically performing an axillary lymph node dissection known as lymphadenectomy. In this open surgical procedure, a relatively large incision (5–10 cm), is made at the axilla (the armpit). Through this incision, a relatively large volume (15 to 30 grams) of fatty tissue and lymph node tissue are removed.

During this process, anywhere from 10 to 30 lymph nodes can be recovered and submitted to pathology, where each of these lymph nodes is examined for the presence or absence of metastatic breast cancer. Based on positive lymph node findings, systemic therapy will be given to the patient with breast cancer, including chemotherapy. If, on the other hand, the lymph nodes of the axilla are free of metastatic disease, then the use of systemic therapies is limited.

Surgical lymphadenectomy carries a low mortality, but high morbidity. The most common morbidity is the development of lymph edema in the arm, which is ipsilateral to the axilla dissected. The development of lymph edema in the ipsilateral arm is, at times, a debilitating complication. Another frequent complication of surgical lymphadenectomy is injury to sensory nerves in the region of the incision, resulting in permanent loss of sensation to the patient, and often in a disfiguring condition termed "winged scapula".

It has been shown in the examination of lymphatic drainage of melanoma, and now shown in the lymphatic drainage of breast cancers, that lymphatic dranage patterns can be defined by the injection of a radioisotope (or other traceable marker such as blue dye) immediately adjacent to the tumor. The isotope (or dye) is then followed, either visually, with a game camera imaging system, or with a Geiger counter-type of counting system The spread of cancer cells is orderly, the first lymph node reached by the drinage channels from the infected breast containing the most cancer cells. Consequently, the first lymph node in the draining system is referred to as the "sentinel" lymph node.

It has been further shown, if one simply removes the sentinel lymph node, the determination of whether or not breast cancer has metasasized to the regional lymph nodes of the axilla can be established without excision of the remaining lymph nodes in the axilla. The surgical removal of only one lymph node greatly reduces the complications of lymph node surgery including the morbidity of lymph edema.

It would be desirable to further reduce the morbidity of the axillary sentinel lymph node biopsy if instrumentation were available to allow the sentinel lymph node to be identified and removed percutaneously with as little effect as possible to the surrounding tissue structure. The apparatus described in this patent can be introduced percutaneously through a small skin opening and directed to the sentinel lymph node thus eliminating open surgical exploration. Consequently, sentinel lymph node biopsy could be accomplished as an office procedure, eliminating hospitalization and minimizing the recovery period.

The elements of a percutaneous sentinel lymph node biopsy are as follows: The tumor site in the breast is injected with a radioisotope (such as technicium 99 m labeled sulfur colloid) which travels via the lymphatic channels to the sentinel lymph node. The sentinel lymph node then becomes radioactively visible, or "hot." The apparatus hereafter described is able to identify or locate the radioactive lymph node through auditory and other signals, indicating when the apparatus is adjacent to the sentinel lymph node. The apparatus is further able to then characterize or "visualize" the surrounding tissue with the associated ultrasound portion of the apparatus. It is important to identify the associated structures adjacent to the lymnph node, because relatively large blood vessels (arteries, veins,) and nerves traverse the axilla. With the combination of both Geiger counter and ultrasound identification, the sentinel lymph node can be identified and biopsied without entering a major blood vessel or severing a major nerve.

With a small entry site, no suturing is required (the procedure is percutaneous), and the patient may be sent home with a simple band-aid over the axillary entry site. The following day, the patient receives the results of the percutaneous sentinel lymph node biopsy determining whether or not metastatic disease is present or absent in the sentinel lymph node draining the affected breast.

Instruments are known in the prior art which could be adapted to perform some of the procedures outlined above. For example, U.S. Pat. No. 5,111,828 to Komberg et al. discloses a percutaneous excisional breast biopsy device having a cannula, open distal and proximal ends, and a sharp cutting surface on the distal end A stylet extends through the cannula and includes a distal puncturing end A localization guide wire is used to direct the instrument to a biopsy site. The cannula is moved distally to cut a desired tissue specimen, after which a descending element is pushed to the distal end of the tissue specimen, then pulled proximally to sever the specimen completely from surrounding tissue.

A significant disadvantage of the Komberg approach is that only one tissue sample may be obtained for each insertion of the instrument into the patient's body to the biopsy site. Once the descending element has been pulled to sever the tissue sample, there is no opportunity to repeat the procedure while the instrument remains in place.

The present invention lacks the disadvantages and shortcomings of the prior art and provides an improved method and device for percutaneous excisional tissue biopsy. The present invention may be used for purposes others than percutaneous biopsy. For example, the device may be used for general organ and tissue removal through a trocar to perform various laparoscopic procedures including splenectomy, nephrectomy, appendectomy and liver removal. The device may also be used laparascopically through a trocar to remove abnormal growths such as polyps.

SUMMARY OF THE INVENTION

This invention provides an inventive tissue sampling probe which offers many advantages over probes available in the prior art. Unexpectedly superior results are obtained in connection with the retrieval of intact tissue specimens, because of a unique combination of cutting features, including, in particular, the employment of an electrosurgical cutting element which is extendible to permit ready severance of the distal end of the tissue specimen, without impact to surrounding tissue. Additionally, the inventive instrument may be advantageously designed so that portions of the instrument which contact the patient's tissue or discharge (i.e. blood) during a procedure are modular and disposable, to permit ready replacement of those portions with a new module for an ensuing procedure, without the necessity of cleaning and sterilizing the instrument. The versatility of the invention permits its use in many applications, including, for example, breast biopsies, intraoperative staging, laparoscopic surgery, and lymphadenectomy procedures.

More particularly, in one aspect of the invention, a tissue sampling apparatus is provided which comprises a tubular body having a primary lumen for receiving a tissue sample, wherein the tubular body has a distal end and a proximal end An electrosurgical cutting element, preferably a wire, is disposed along an axial length of the tubular body. The cutting element includes a distal cutting end and is axially slidable between an axially extended position and an axially retracted position relative to the tubular body. The instrument is particularly suited to axial cutting when the wire is retracted, as it is advanced distally through a tissue region from which a tissue sample is desired. When the wire is extended, it curves in a radial direction across a portion of the transverse dimension of the distal end of the tissue specimen, so that, as the tubular body is slowly rotated, the curved distal end of the cutting wire functions to cleanly sever the distal end of the specimen from the remaining tissue without impacting the remaining tissue.

In another aspect of the invention, a tissue sampling apparatus is provided which comprises a tubular body having a primary lumen for receiving a tissue sample, having a distal end and a proximal end, wherein the tubular body is comprised of disposable materials. The apparatus further comprises an electrosurgical cutting element which is disposed along an axial length of the tubular body, and a housing for enclosing a portion of the tubular body, wherein the housing comprises a lid portion which is openable relative to a body portion of the housing. Advantageously, the tubular body is constructed in a modular fashion, so that it may be removed from the housing by opening the lid portion, and readily replaced by another tubular body module between medical procedures.

In still another aspect of the invention, a method of capturing a body tissue sample is disclosed, wherein a tissue sampling apparatus comprising a tubular body having a lumen extending therethrough and a distal end is utilized. An electrosurgical cutting element having a distal end portion which is disposed distally of the distal end of the tubular body, and an actuator for moving (advancing and retracting) the cutting element, are also disposed on the tissue sampling apparatus. The method comprises the steps of energizing the electrosurgical cutting element using an electrocautery generator, and rotating the tubular body at a relatively high rate of speed. Then the tubular body is advanced through a tissue portion a desired distance so that the energized electrosurgical element cuts a generally cylindrical tissue sample as the tissue sample enters the lumen. In essence, the distal end of the tubular body receives (captures) the cylinder of tissue created as the tube and electrosurgical element are energized, rotated, and axially advanced simultaneously. Once the desired tissue sample length has been achieved, distal advancement of the instrument is halted, and the electrosurgical cutting element is advanced linearly so that the distal end portion thereof extends radially inwardly across a portion of a distal end of the tissue sample core. Preferably simultaneously, the tubular body is rotated at a relatively low rate of speed, so that the distal end portion of the electrosurgical cutting element severs the tissue sample core from the tissue portion.

The invention, together with additional features and advantages thereof, may best be understood by reference to the following description taken in conjunction with the accompanying illustrative drawing.

BRIEF DESCRIPTION OF THE DRAWING

FIG. 1 is a perspective view of a fist preferred embodiment of the inventive tissue sampling instrument;

FIG. 2 is a side view, in elevation, illustrating a tissue specimen entering the distal end of the inventive instrument shown in FIG. 1;

FIGS. 3–8 are schematic side views of the distal end of the inventive instrument shown in FIG. 1, illustrating sequentially the relative position of the electrocautery cutter during a representative tissue specimen capturing procedure;

FIG. 9 is an enlarged view, in cross-section, of a portion of the distal end of the inventive instrument designated by the letter A in FIG. 1;

FIG. 14 is a perspective view of the embodiment illustrated in FIG. 11, showing operation of the tissue sampling embodiment as it approaches a tissue region to be sampled;

FIG. 15 is a perspective view of a stand-alone sensing probe which may be used in connection with either of the embodiments of FIGS. 1 or 11; and FIGS. 16, 16a, and 16b are perspective views of a multi-vision probe which may be used in connection with the embodiments of FIGS. 1 or 11.

DESCRIPTION OF THE INVENTION

Figure 10:
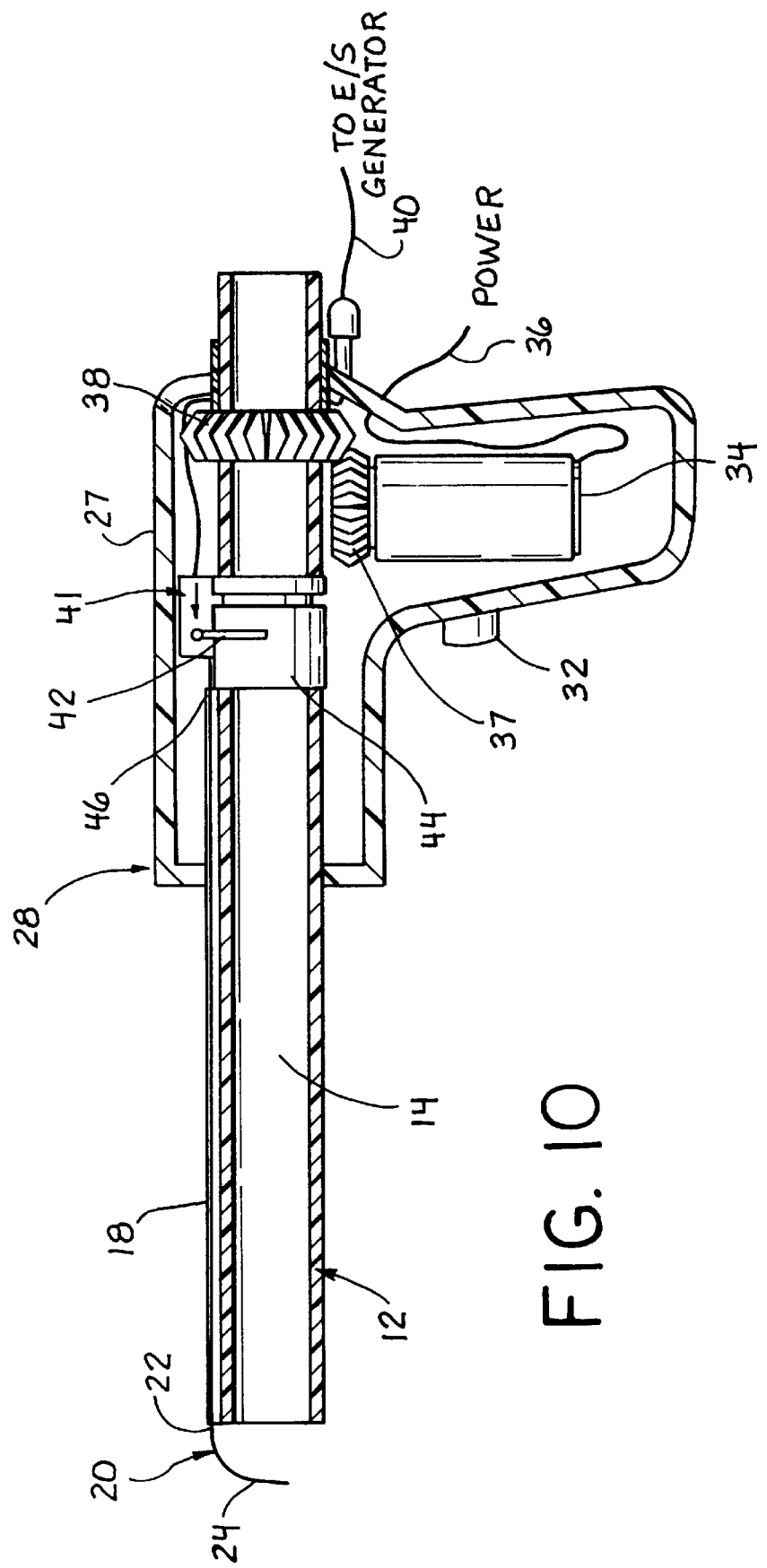
FIG. 10 is a side view, in cross-section, of the inventive instrument illustrated in FIG. 1.

Referring now more particularly to FIGS. 1 and 9, a first embodiment of the invention is shown. The inventive tissue sampling probe 10 comprises a tube 12 having a lumen 14. A cutter channel 16 extends axially along the length of the tube outer wall 18 (FIG. 9). Extending axially through the cutter channel 16 is an electrocautery cutter wire 20, preferably comprised of an electrically conductive shaped metallic memory wire, such as Nitinol, which comprises a proximal portion 22 and a distal portion 24. The cutter wire 20 is preferably formed as a flattened round wire, because the resultant rectangular shape, which makes the wire stiff in the x-direction and flexible in the y-direction, is preferred for resisting lateral forces which are encountered as the wire is rotated in tissue.

The tube 12 preferably comprises an inner layer 25 and an outer layer 26 (FIG. 9), the inner layer 25 being preferably fabricated of a non-conductive radiolucent or radiodense biocompatible composite material, such as a glass filament wound epoxy impregnated matrix material. Another possibility is to utilize a high density polyethylene (HDPE), which is crosslinked with a high radiation dose, so that it behaves like a thermoset rather than a thermoplastic. The tube 12 preferably has a round cross-section, though other tube shapes may be used as well. Advantageous characteristics of the preferred composite material include light weight, high melt temperature, high dielectric, ductility, non-conductivity, and machinability. An outer layer 26 may be employed, the outer layer preferably comprising a high dielectric coating which is shrink wrapped about the outer diameter of the inner layer 25. Because the preferred material for the inner layer 25 is easily machinable, the channel 16 is preferably machined into the outer surface of inner layer 25.

Disposed proximally of the tube 12 is an actuator 27, which preferably comprises a housing 28, a fixed handle 29, a cutter advancement slide knob 30, and an actuation switch 32. As illustrated in FIG. 10, the housing 28 encloses a variable speed electric motor 34 which is connected to a power supply via a power cord 36. Operation of the motor 34 drives interengaging gears 37 and 38, resulting in selective rotation of the tube 12.

An important aspect of the invention is the use of an electrocautery generator (not shown). The electrical energy from the electrocautery (electrosurgical) generator is conducted along an electrical line 40 to the cutter wire 20, and is selectively activated or deactivated using the electrosurgical energy actuation switch 32. As illustrated in FIG. 10, the electrical line 40 is connected to an electrode advancement collar 41, which comprises an electrical contact brush 42 and an electrode ring 44. A proximal end 46 of the cutter wire (electrode) 20 is attached to the electrode advancement collar. The cutter advancement slide knob 30 is mechanically attached to the electrode advancement collar 41. Thus, the electrode 20 is advanced distally when the cutter advancement slide knob 30 is moved distally. For safety reasons, the slide knob 30 and the electrode advancement collar 41 are electrically insulated from the cable 40, brush 42, and electrode ring 44.

In operation, with respect to the embodiment of FIG. 1, the electrocautery generator is activated using the actuation switch 32 to electrically activate the cutter wire 20. The switch 32 is preferably a momentary switch, which is actuated only when depressed and held by an operator. Simultaneously, the switch 32 actuates the motor 34 to cause the tube 12 to rotate at a relatively high rate of speed by means of gears 37, 38. Then, the tube 12 is advanced by the operator through tissue with the cutter wire 20 in its retracted position, as shown in FIG. 3, to obtain the desired tissue sample. With the wire 20 energized to function as an electrocautery cutter, the advancement of the rotating tube 12 easily slices through the tissue to create a tissue specimen 48 (FIG. 1) for capture within the lumen 14. In the preferred embodiment, depth marks (not shown) may be disposed axially along the exterior surface of the tube 12 in order to assist the physician in determining when the tube 12 has been advanced to the desired position.

In its preferred operational mode, the energized conductive cutter wire 20 functions to define and cut a tissue sample 48 having approximately the same internal diameter or crosssectional shape as that of the tube 12. The distal end of the tube 12 receives the generally cylindrical tissue sample, which is created as the tube and cutter wire are energized, rotated, and axially advanced simultaneously. Once a sample of adequate length has been secured, advancement of the tube 12 is halted, and the cutter wire 20 is advanced distally relative to the tube 12 by sliding the cutter advancement slide knob 30 distally. Distal advancement of the cutter wire 20 is illustrated sequentially in FIGS. 4, 5, and 6. As shown in FIG. 6, the cutter wire 20 is fully advanced so that the electrically energized distal end 24 is curved radially inwardly to sever a portion of the distal end 49 of the tissue specimen 48 (FIG. 2). While the wire 20 is in its fully advanced position, the tube 12 is rotated at a relatively slow rate of speed, by operation of the motor 34, until the tube 12 has been rotated at least 180 degrees, to the position illustrated in FIG. 7, and preferably 360 degrees, to the position illustrated in FIG. 8. In order to rotate the tube 12 at the second lower rate of speed, either the switch 32 may be actuated to a second operating position, or a second switch may be utilized. This slow rotation of the tube 12 permits the energized distal end 24 of the cutter wire 20 to sever the entire distal end 49 of the tissue specimen 48, thereby capturing the entire specimen 48 within the lumen 14 of the instrument 10, as shown in FIGS. 1 and 2.

Once the tissue specimen has been captured within the lumen 14, one or more additional samples may be obtained and accommodated within the lumen if desired. When the desired tissue samples have been obtained, the instrument may be removed from the patient's body so that the tissue sample(s) may be extracted and examined. In order to expedite tissue sample capture, the interior surface of the tube 12 may be coated to reduce frictional contact between the tube and the tissue sample as it travels through the lumen 14.

Though in the preferred embodiment, it is not necessary to utilize a source of suction (vacuum) in order to actively draw the tissue sample into the tubular body 12, it is feasible, and in some instances desirable, to do so, in a manner similar to that disclosed in parent application Ser. No. 08/705,622. In such an instance, a source of vacuum pressure would be employed for drawing a vacuum through the primary lumen 14, so that the vacuum pressure in the primary lumen draws tissue to be sampled into the primary lumen as the electrosurgical cutting element 20 cuts the drawn tissue. The vacuum pressure may then act to assist transport of the tissue specimen proximally through the primary lumen to a tissue receptacle.

Figure 11:
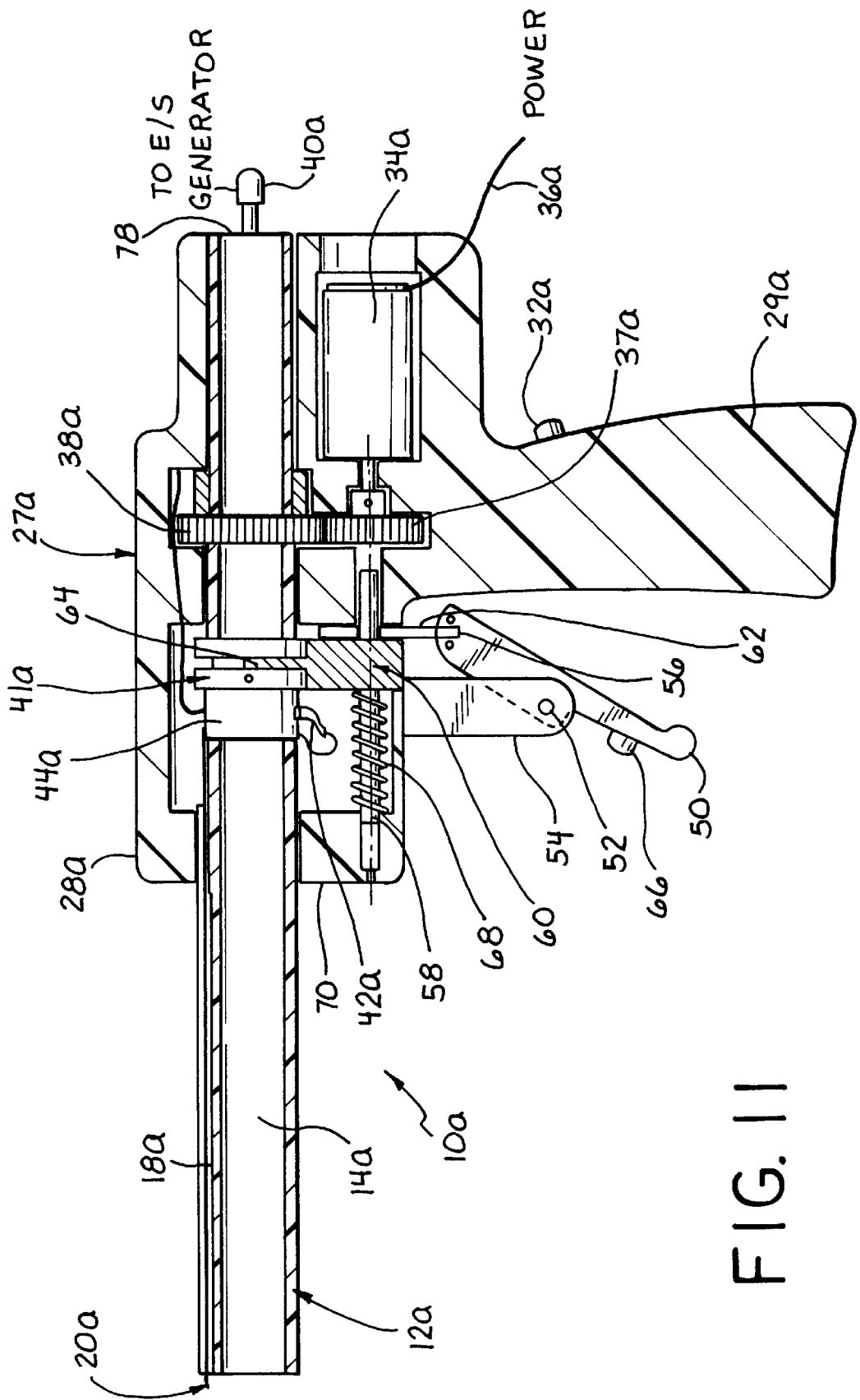
FIG. 11 is a side view, in cross-section, of a second preferred embodiment of the inventive tissue sampling instrument.
Figure 12:
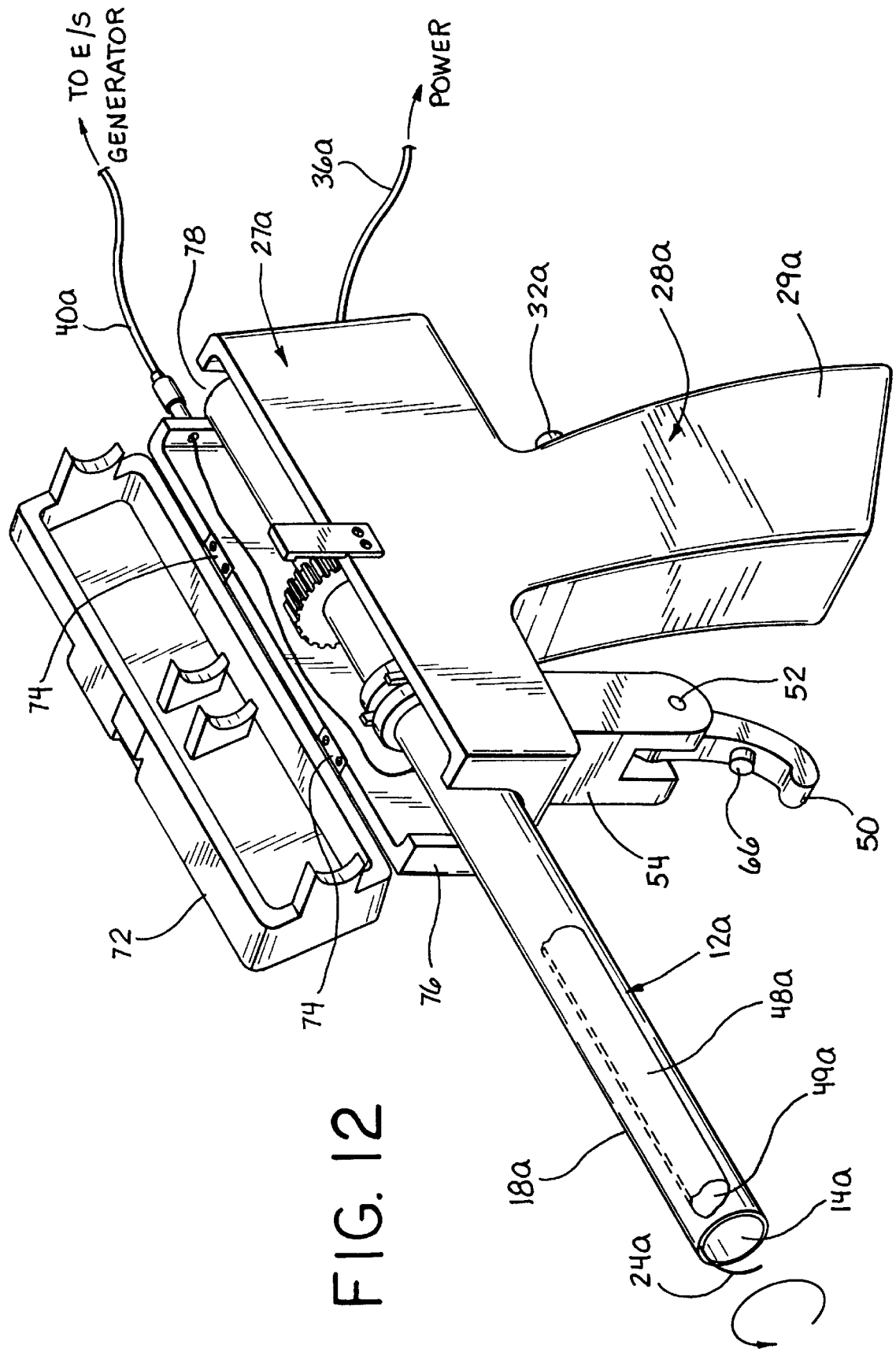
FIG. 12 is a perspective view of the inventive embodiment illustrated in FIG. 11.

Many other embodiments may be employed other than the embodiment illustrated in FIG. 1. For example, a modified embodiment, which is presently preferred, is illustrated in FIGS. 11 and 12, wherein all elements corresponding to those of the embodiment of FIG. 1 are designated by like reference numerals, succeeded by the letter "a". In this embodiment, a modified actuation system is employed. The modified actuation system includes a first actuation switch 32a, disposed on a proximal surface of the handle 29a, which is preferably a momentary switch (actuated only when physically depressed and held by the operator). The first actuation switch 32a simultaneously actuates the motor 34a to rotate the tube 12a at a relatively high rotational velocity, and energizes the cutter wire 20a for electrosurgical cutting. Additionally, a cutter wire advancement trigger 50 is provided distally of the handle 29a. The cutter wire advancement trigger 50 is pivotally mounted, via pivot pin 52, to a fork 54, as illustrated in FIGS. 11 and 12, and is attached at its upper end to an electrode advancement plate 56 (FIG. 11). Such attachment between the trigger 50 and the advancement plate 56 may be by means of any conventionally known mechanical fastening system In turn, the electrode advancement plate is slidably disposed on a carriage pin 58, and is disposed between an electrode carriage block 60 and a proximal surface 62 of the housing 28a, the carriage block 60 also being slidably disposed on the carriage pin 58. An upper portion 64 of the carriage block 60 is fixedly attached to the electrode advancement collar 41a. A second actuation switch 66 is disposed on the trigger 50. The switch 66 is adapted to simultaneously energize the cutter wire 20a and to actuate the motor 34a to rotate the tube 12a, as is the first switch 32a, except that when the second switch is actuated, the motor operates at a lower speed to rotate the tube 12a at a relatively low rotational velocity. A biasing spring 68 is disposed on the carriage pin 58, between the carriage block 60 and a distal portion 70 of the housing 28a, to bias the carriage block 60 proximally, so that the cutter wire (electrode) 20a is biased to its retracted position.

Figure 13A:
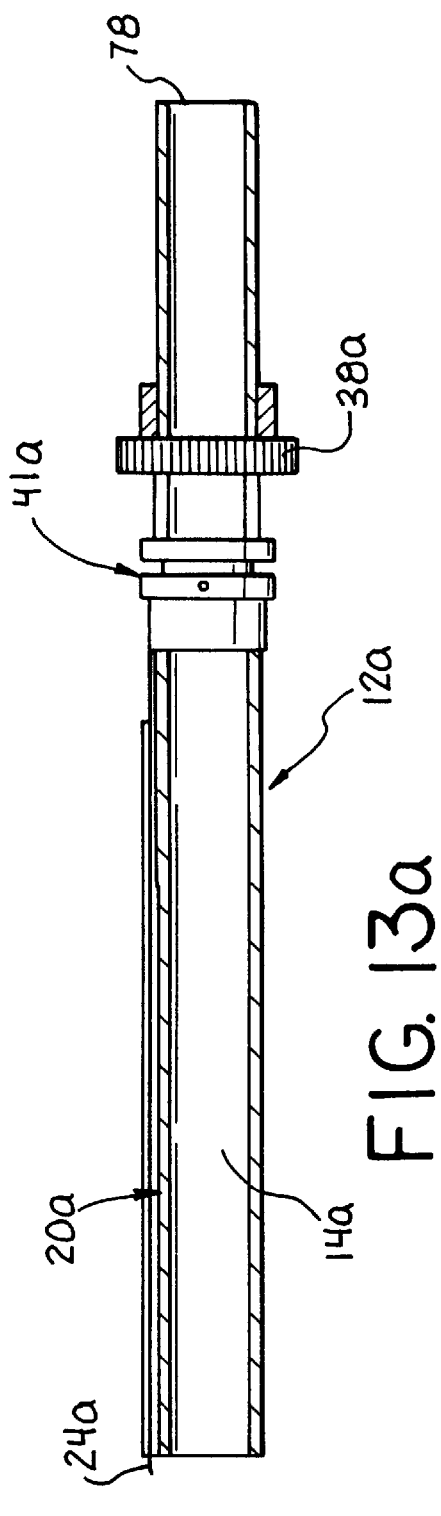
FIGS. 13a and 13b are cross-sectional views illustrating, in isolation, the tube portion of the tissue sampling instrument embodiment shown in FIG. 12.
Figure 13B:
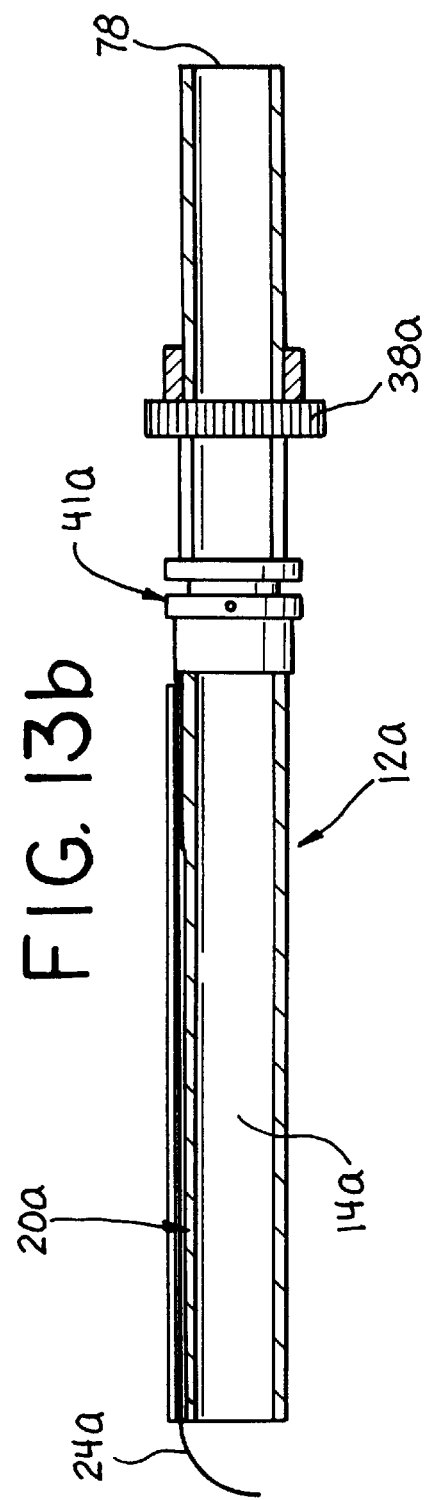

An advantageous feature of the inventive embodiment of FIGS. 11 and 12 is that it is adapted to have a modular construction, so that portions of the instrument having physical contact with a patient's tissue and/or blood during a medical procedure may be disposed of and readily replaced by a practitioner. This modularity permits expedited reuse of the instrument for another patient procedure without the necessity for extensive cleaning and sterilization. In particular, the housing 28a is constructed to comprise a lid 72 which is attached by means of hinges 74 to the main housing portion 76 so that the housing 28a is openable to permit access to the entire tube portion 12a. When closed, the lid 72 is secured by a latch 78. Thus, the entire tube portion 12a, as illustrated in FIGS. 13a and 13b, may be readily installed in or removed from the housing 28a of the instrument 10a by a practitioner or an assistant between procedures. The entire tube portion 12a, including the electrode advancement collar 41a and the gear 38a, is preferably constructed of disposable materials, such as biocompatible plastics or composite materials, so that it may be made disposable after a single use for a reasonable cost.

In operation, with reference to FIGS. 11–13b, a practitioner desiring to obtain a particular tissue sample from a patient may grasp the handle 29a of the instrument 10a and move the instrument 10a toward the targeted entry point on the patient's body using known imaging techniques. As the distal end of the tube 12a approaches entry into the body of the patient, switch 32a is actuated by the practitioner depressing and holding same so that the cutter wire 20a is energized and the motor 34a is simultaneously actuated to rotate the tube relatively quickly, in order to enhance the cutting process. During the ensuing period of time, the instrument continues to be advanced through the patient's tissue, with the cutter wire 20a biased by spring 68 to its retracted position, as illustrated in FIG. 13a, until a tissue specimen 48a of a desired length is captured within the lumen 14a of the tube 12a With the wire 20a energized and retracted, and the tube 12a rotating at a relatively high rotational velocity, the entire distal end of the tube 12a functions effectively as a cutting element to readily obtain a tissue sample core from the desired tissue area. Again, as in the first embodiment, depth marks (not shown) may be disposed axially along the exterior surface of the tube 12a to assist the physician in determining when the tube 12a has been advanced to the desired position.

In its preferred operational mode, the energized conductive cutter wire 20a functions to cut a tissue sample 44a having approximately the same diameter or cross-sectional shape as that of the inside diameter of tube 12a. Once a sample of adequate length has been secured, advancement of the instrument 10a is halted, and the cutter wire 20a is advanced by depressing the cutter wire advancement trigger 50 so that it pivots proximally about the pivot pin 52, from the position shown in FIG. 11 to the position shown in FIG. 12. This pivoting motion causes the electrode advancement plate 56 to move distally, thereby contacting the carriage block 60 and pushing it distally as well, against the bias of the spring 68. This movement of the carriage block 60 in turn causes the electrode advancement collar 41a to slide distally, thereby extending the electrode (cutter wire) 20a to its extended position, as shown in FIGS. 12 and 13b. Contact of the electrode advancement plate 56 with the fork 54 serves as a stop, to ensure that the cutter wire 20a is only advanced a desired distance to create the curved portion 24a for severing the distal end of the specimen 48a.

Advantageously, as the practitioner's fingers grip the trigger 50 and depress it proximally to advance the cutter wire 20a, the switch 66 is simultaneously depressed, thereby actuating the motor 34a to rotate the tube 12a at a relatively slow rotational velocity, as opposed to the relatively high rotational velocity initiated by actuation of the switch 32a. Depression of the switch 66, which is preferably a momentary switch (like switch 32a), also simultaneously energizes the cutter wire 20a to initiate an electrosurgical cutting capability. Applicants have found that the ability to simultaneously advance the cutting wire 20a distally and to slowly rotate the tube 12a is beneficial to the tissue capture process, relative to the alternative of first extending the wire to its advanced position, and then initiating rotation of the tube 12a, which was originally thought to be necessary in order to prevent excessive lateral stresses (torque) on the cutting wire as it is being extended, due to the rotation of the tube 12a.

Once the cutter wire 20a is energized and fully advanced to its extended position, with the tube 12a rotating relatively slowly, due to actuation of the switch 66, as illustrated in FIGS. 12 and 13b, the energized distal end 24a of the wire 20a functions to sever the entire distal end 49 of the tissue specimen 48a, as in the first embodiment illustrated in FIG. 1. Once severed, the tissue specimen is completely captured within the lumen 14a of the instrument 10a (FIG. 12), and the instrument may be withdrawn from the patient's body to retrieve the specimen for examination. Alternatively, a source of vacuum could be employed to assist in drawing tissue into the tube 12a and/or to assist in transporting the tissue specimen proximally through the tube 12a into a tissue receptacle (not shown).

In order to expedite preparation of the instrument for another procedure on a different patient, once the specimen 48a has been retrieved, the lid 72 of the housing 28a may be opened, and the used module 12a separated from the instrument and discarded as medical waste. Then, a new module 12a may be installed within the housing, and the lid secured in a closed position. Of course, the instrument may be used multiple times on the same patient without sterilization or replacement of the disposable module.

A particularly advantageous aspect of the invention is its ability to be used in connection with sensing probes for identifying and locating desired tissue to be sampled. For example, ultrasound probes or radiation detecting (Geiger) probes may be employed, such as those disclosed in U.S. Pat. Nos. 4,959,547, 5,036,201, 5,119,818, 5,148,040, 5,170,055, and 5,246,005, which are assigned to Care Wise Medical Products Corporation of Morgan Hill, Calif., and are herein expressly incorporated by reference. Referring particularly now to FIGS. 15–16b, the instrument 10a illustrated in FIG. 11 is shown, though the instrument 10 illustrated in FIG. 1 or other similar instruments could be substituted therefor. As illustrated in FIGS. 11, 12, 13a, and 13b, the proximal end 78 of the tube 12a is open, so that there is a sight line through the entire lumen 14a of the tube 12a, from the proximal end 78 to the distal end of the tube 12a. The proximal end 78 may be configured to receive a sensing probe 80 or 82 (FIGS. 15 and 16).

A stand alone sensing probe 80 is illustrated in FIG. 15, which may comprise either an ultrasonic probe or a geiger probe, both of which are conventionally known in the medical diagnostic arts. The probe 80 is specifically configured to mate into the through hole 78 of the soft tissue acquisition device 10a. Electronic control lines 84 extend from a proximal end of the probe 80 to appropriate control units, for receiving and processing information obtained by the probe.

Alternatively, a multi-vision probe, such as the probe 82 illustrated in FIG. 16, may be utilized. This type of probe is capable of functioning both as an ultrasonic probe and as a geiger probe, and has two sets of control lines 86 and 88 for communicating with ultrasonic and geiger electronic control units, respectively.

In operation, a lesion (tissue) 90 to be sampled (FIG. 15) is located using a multivision probe 82 or a combination of stand-alone probes 80, which are disposed in the soft tissue acquisition device 10a. The geiger portion of the probe provides an X-Y location on the surface of the tissue to be sampled, while the ultrasonic portion provides depth information as well as X-Y location information. Then, the soft tissue acquisition device 10a is held in position, while the sensing probe(s) is (are) removed. Following removal of the sensing probe, a tissue sample may be obtained using the methods described supra.

While this invention has been described with respect to various specific examples and embodiments, it is to be understood that the invention is not limited thereto and that it can be variously practiced within the scope of the following claims.

What is claimed is:

1. A tissue sampling apparatus, comprising:
   a tubular body having a primary lumen for receiving a tissue sample, and having a distal end and a proximal end, said lumen having a cross-sectional area;
   an electrosurgical cutting element disposed along an axial length of said tubular body, said cutting element including a distal cutting end and having an axially extended position and an axially retracted position relative to said tubular body;
   wherein the distal cutting end of the electrosurgical cutting element is disposed transversely to extend across a portion of the cross-sectional area of said lumen when the cutting element is in said axially extended position, and is not disposed to extend across the cross-sectional area of said lumen when the cutting element is in said axially retracted position.

2. The tissue sampling apparatus as recited in claim 1, wherein the electrosurgical cutting element comprises a wire.

3. The tissue sampling apparatus as recited in claim 2, wherein the wire comprises an electrically conductive shaped metallic memory wire.

4. The tissue sampling apparatus as recited in claim 2, wherein the wire cross-section comprises a rectangular shape.

5. The tissue sampling apparatus as recited in claim 1, wherein said tubular body comprises an outer wall, said outer wall having a cutter channel disposed therein, said electrosurgical cutting element being disposed within said cutter channel, wherein when the cutting element is in said axially extended position the distal end thereof extends distally beyond a distal end of the cutter channel and when the cutting element is in said axially retracted position the entire distal end thereof is disposed within said cutter channel.

6. The tissue sampling apparatus as recited in claim 1, wherein the tubular body is comprised of a non-electrically conductive material.

7. The tissue sampling apparatus as recited in claim 1, wherein said tubular body lumen is sized to accommodate a plurality of tissue samples.

8. The tissue sampling apparatus as recited in claim 1, and further comprising a coating on an interior surface of the tubular body to facilitate transport of tissue samples therethrough.

9. The tissue sampling apparatus as recited in claim 1, and further comprising depth marks on said tubular body to facilitate positioning of the apparatus in a patient's body.

10. The tissue sampling apparatus as recited in claim 1, wherein said tubular body is rotatable at two different rotational velocities, said tissue sampling apparatus further comprising a first actuation switch for energizing said electrosurgical cutting element and rotating said tubular body at a first higher rotational velocity when said electrosurgical cutting element is in said axially retracted position, and a second actuation switch for energizing said electrosurgical cutting element and rotating said tubular body at a second lower rotational velocity when said electrosurgical cutting element is in said axially extended position.

11. The tissue sampling apparatus as recited in claim 1, wherein said tubular body is rotatable, said tissue sampling apparatus further comprising a pivotable trigger, said trigger being adapted to move said electrosurgical cutting element to the axially extended position and to simultaneously rotate said tubular body at a relatively low rotational velocity.

12. The tissue sampling apparatus as recited in claim 1, wherein said tissue sampling apparatus further comprises a housing, said housing having a lid portion which is openable relative to a remaining housing portion, said tubular body being removable from said housing for ready disposal after a single use.

13. The tissue sampling apparatus as recited in claim 1, wherein said tubular body is constructed of inexpensive disposable plastic material.

14. A tissue sampling apparatus, comprising:
    a tubular body having a primary lumen for receiving a tissue sample, and having a distal end and a proximal end, said tubular body being comprised of disposable materials;
    an electrosurgical cutting element disposed along an axial length of said tubular body;
    a housing for enclosing a portion of the tubular body, the housing comprising a lid portion which is openable relative to a body portion thereof;
    said tubular body including a rotational drive portion for interconnecting with a rotational driving mechanism in said housing for selectively rotating said tubular body, wherein said tubular body, including said rotational drive portion, is removable from said housing and readily replaceable by another tubular body between medical procedures.

15. The tissue sampling apparatus as recited in claim 14, wherein said rotational drive mechanism comprises a gear.

16. The tissue sampling apparatus as recited in claim 14, wherein said electrosurgical cutting element comprises a wire which is selectively extendable and retractable along an axis of said tubular body.

17. The tissue sampling apparatus as recited in claim 16, wherein a distal end of said wire curves in a direction generally transverse to said axis when the wire is extended distally.

18. A method of capturing a body tissue sample using a tissue sampling apparatus comprising a tubular body having a lumen extending therethrough and a distal end, an electrosurgical cutting element having a distal end portion which is disposed distally of the distal end of the tubular body, and an actuator for moving the cutting element, the method comprising:
    energizing the electrosurgical cutting element;
    rotating the tubular body at a relatively high rate of speed;
    advancing the tubular body through a tissue portion a desired distance so that the energized electrosurgical element cuts a tissue sample core as the tissue sample enters the lumen;
    advancing the electrosurgical cutting element to an extended position relative to the tubular body so that said distal end portion extends radially inwardly across a portion of a distal end of said tissue sample core; and
    rotating the tubular body at a relatively low rate of speed, so that the distal end portion of the electrosurgical cutting element severs said tissue sample core from said tissue portion.

19. The method as recited in claim 18, wherein the electrosurgical cutting element is advanced to said extended position and the tubular body is rotated at said relatively low rate of speed simultaneously.

20. The method as recited in claim 18, and further comprising the steps of removing the tubular body from the apparatus at the conclusion of a medical procedure, and installing a new tubular body prior to the commencement of another medical procedure.

* * * * *

UNITED STATES PATENT AND TRADEMARK OFFICE
CERTIFICATE OF CORRECTION

PATENT NO. : 5,913,857  
DATED : June 22, 1999  
INVENTOR(S) : Mark A. Ritchart and Minh Tran Page 1 of 1

It is certified that error appears in the above-identified patent and that said Letters Patent is hereby corrected as shown below:

Column 3,
Line 59, "band-aid" should read -- BAND-AID® Brand Adhesive Bandage --.

Signed and Sealed this

Twenty-first Day of May, 2002

Attest:

Attesting Officer

JAMES E. ROGAN
Director of the United States Patent and Trademark Office